(12) United States Patent
Nagase et al.

(10) Patent No.: US 9,963,460 B1
(45) Date of Patent: May 8, 2018

(54) MORPHINAN DERIVATIVE

(71) Applicants: University of Tsukuba, Ibaraki (JP); Nippon Chemiphar Co., Ltd., Tokyo (JP)

(72) Inventors: Hiroshi Nagase, Tsukuba (JP); Naoshi Yamamoto, Tsukuba (JP)

(73) Assignees: University of Tsukuba, Ibaraki (JP); Nippon Chemiphar Co., Ltd., Tokyo (JP)

( * ) Notice: Subject to any disclaimer, the term of this patent is extended or adjusted under 35 U.S.C. 154(b) by 0 days. days.

(21) Appl. No.: 15/463,418

(22) Filed: Mar. 20, 2017

(30) Foreign Application Priority Data

Feb. 10, 2017 (JP) .................................. 2017-023444

(51) Int. Cl.
   *C07D 491/02* (2006.01)
   *A61K 31/445* (2006.01)
   *C07D 489/02* (2006.01)

(52) U.S. Cl.
   CPC .................................. *C07D 489/02* (2013.01)

(58) Field of Classification Search
   CPC ............................ C07D 491/02; A61K 31/445
   USPC .................................. 514/279; 546/41, 43, 46
   See application file for complete search history.

(56) References Cited

U.S. PATENT DOCUMENTS 6,187,782 B1 * 2/2001 Nagase ................ C07D 489/12
                                                             514/279

FOREIGN PATENT DOCUMENTS

| JP | 2525552 B2 | 8/1996 |
|----|------------|--------|
| JP | 2008179554 A | 8/2008 |
| JP | 2009196933 A | 9/2009 |
| WO | 2008100977 | * 8/2008 |

OTHER PUBLICATIONS

Hayashida et al., Tetrahedron (2011), 67(35), 6682-6688.*
Yamaotsu et al., Bioorganic & Medicinal Chemistry (2010), 18(12), 4446-4452.*
Nagase et al., Bioorganic & Medicinal Chemistry Letters (2010), 20(1), 121-124.*
Fujii et al., Current Medicinal Chemistry (2006), 13(10), 1109-1118.*
Fujii et al., Bioorganic & Medicinal Chemistry Letters (2004), 14(16), 4241-4243.*
Fujii et al., Bioorganic & Medicinal Chemistry (2004), 12(15), 4133-4145.*

* cited by examiner

*Primary Examiner* — Niloofar Rahmani
(74) *Attorney, Agent, or Firm* — Wood Herron & Evans LLP

(57) ABSTRACT

A morphinan derivative represented by the following formula (I), a tautomer or a stereoisomer of the compound, or a pharmaceutically acceptable salt thereof, or a solvate thereof, and a medicament, an analgesic and an antipruritic drug including the same as an active ingredient:

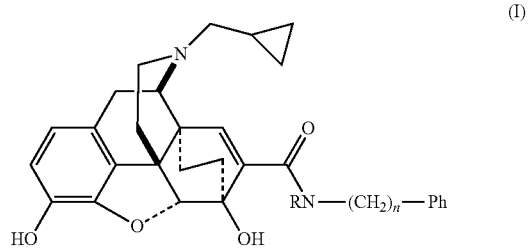

(I)

wherein R is selected from hydrogen and $C_{1-6}$ alkyl, and n represents an integer of 0 to 2.

15 Claims, 1 Drawing Sheet

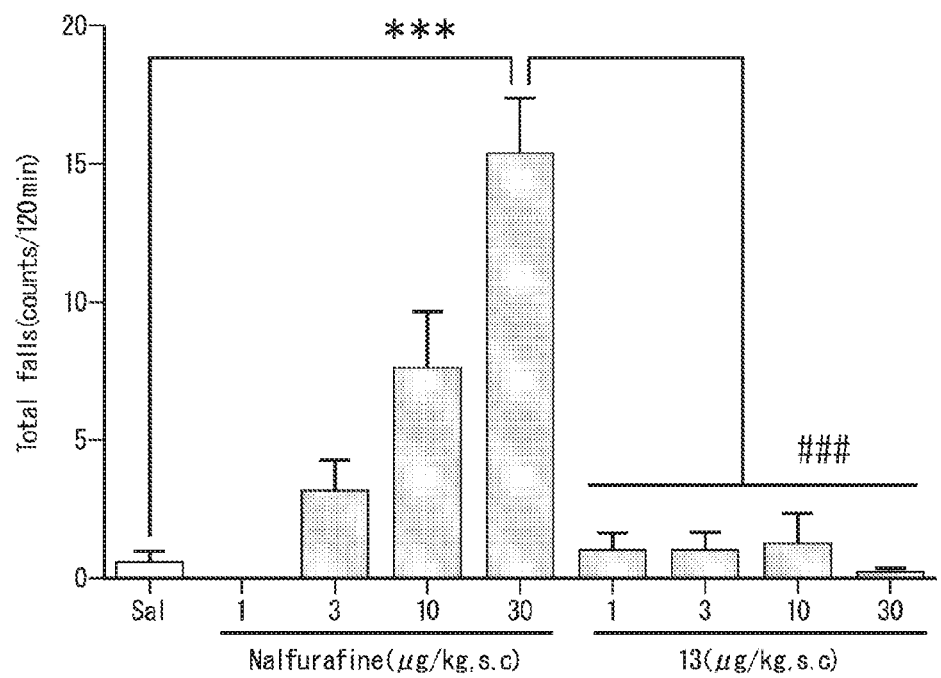

MORPHINAN DERIVATIVE

BACKGROUND OF THE INVENTION

Field of the Invention

The present invention relates to morphinan derivatives having an opioid κ receptor agonist activity.

Priority is claimed on Japanese Patent Application No. 2017-023444, filed Feb. 10, 2017, the content of which is incorporated herein by reference.

Description of Related Art

Three types of opioid receptor including μ, δ, and κ receptors are known. Morphine with strong affinity to the μ receptor has been used as an analgesic for a long time. However, opioid receptor agonists are known to cause adverse events such as drug dependence, respiratory depression and constipation or the like via the μ receptor.

On the other hand, κ receptor agonists are also known to have analgesic effect while not being involved in the adverse events observed in morphine.

Meanwhile, κ receptor agonists are generally known to have sedative effect and drug aversive effect. Nalfurafine serves as the only example of a κ receptor agonist without aversion. However, the sedative effect induced by nalfurafine at an analgesic dose, change the indication to an antipruritic drug, but no κ receptor agonists have yet been approved as an analgesic.

Accordingly, κ receptor-selective agonists with no sedative effect and drug aversive effect are expected as drugs for treating, ameliorating or preventing diseases by using the opioid κ agonists, including an analgesic.

Japanese Unexamined Patent Application, First Publication No. 2008-179554 describes a compound represented by the following formula (A) selectively binds to the opioid κ receptor:

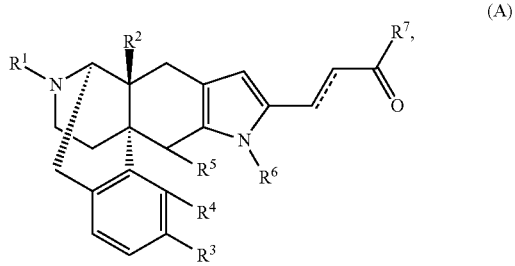

However, the selectivity thereof was still insufficient.

Further, compounds represented by the following formula (B) are reported in Japanese Unexamined Patent Application, First Publication No. 2009-196933:

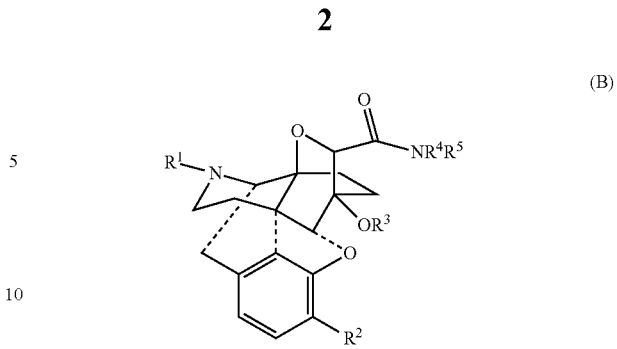

It is described that these compounds selectively bind to the opioid κ receptor and afford analgesic effect. However, the analgesic activity thereof was not satisfactory.

On the other hand, a compound (nalfurafine) represented by the following formula (C) is reported in Japanese Patent Publication No. 2525552:

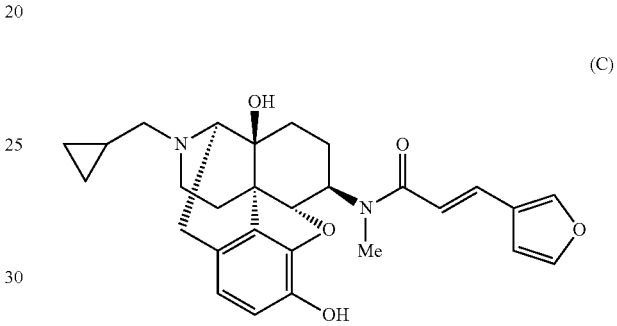

It is described that this compound has potent analgesic activity induced by the opioid κ receptor. However, since sedative effect was shown at an analgesic dose, the nalfurafine was not applied to thereof an analgesic.

Accordingly, opioid κ selective agonists which has clinically useful, and has a potent analgesic effect have not been known.

SUMMARY OF THE INVENTION

An object of the present invention is to provide a drug with a reduced sedative and aversive effect, which is effective in treating, ameliorating or preventing various diseases by use of the opioid κ receptor agonists.

Under such circumstances, the inventors of the present invention engaged in intensive studies and, as a result, found that specific morphinan derivatives have high selectivity for κ opioid receptor and potent agonist activity, thereby completing the present invention.

That is, the present invention relates to morphinan derivatives represented by the following formula (I):

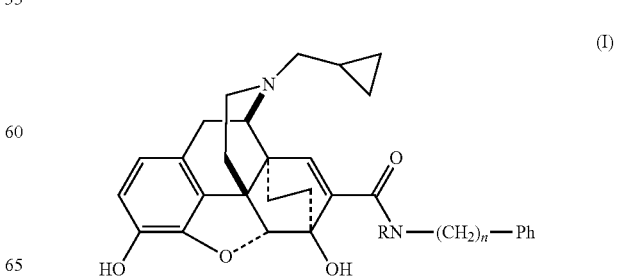

(wherein R is selected from hydrogen and $C_{1-6}$ alkyl, and n represents an integer of 0 to 2), a tautomer or a stereoisomer of the each compound, a pharmaceutically acceptable salts thereof or solvates thereof.

Further, the present invention relates to a pharmaceutical composition containing morphinan derivatives represented by the above formula (I), a tautomer or a stereoisomer of the compound, a pharmaceutically acceptable salts thereof or solvates thereof as active ingredients.

Furthermore, the present invention relates to an drug for treating, ameliorating or preventing a disease by using opioid κ receptor agonists, containing morphinan derivatives represented by the above formula (I), a tautomer or a stereoisomer of the each compounds, pharmaceutically acceptable salts thereof or solvates thereof as active ingredients.

Moreover, the present invention relates to an analgesic containing morphinan derivatives represented by the above formula (I), a tautomer or a stereoisomer of the each compounds, pharmaceutically acceptable salts thereof or solvates thereof as active ingredients.

Further, the present invention relates to an antipruritic drug containing morphinan derivatives represented by the above formula (I), a tautomer or a stereoisomer of the each compounds, pharmaceutically acceptable salts thereof or solvates thereof as active ingredients.

BRIEF DESCRIPTION OF THE DRAWINGS

FIG. 1 is a diagram illustrating results of sedative effects confirmation test according to a rotarod test.

DETAILED DESCRIPTION OF THE INVENTION

Hereinafter, the present invention will be described in further detail.

Preferred embodiments of the morphinan derivatives represented by the above formula (I), a tautomer or a stereoisomer of the compound, a pharmaceutically acceptable salt thereof or a solvate thereof include the following.

R represent hydrogen or a $C_{1-6}$ alkyl group, here, the $C_{1-6}$ alkyl group is preferably a linear alkyl group such as a methyl group, an ethyl group, a propyl group or the like, or a branched alkyl group such as an isopropyl group, an isobutyl group, a tert-butyl group or the like, and a methyl group is preferred. n represents an integer of 0 to 2, and is preferably 1.

In the morphinan derivatives represented by the above formula (I), a tautomer or a stereoisomer of the compound or a pharmaceutically acceptable salt thereof, preferable examples of the pharmaceutically acceptable salt include an acid addition salt, and examples of the acid addition salt include (i) salts with mineral acids such as hydrochloric acid, sulfuric acid, phosphoric acid, and the like, (ii) salts with organic carboxylic acids such as formic acid, acetic acid, citric acid, trichloroacetic acid, trifluoroacetic acid, fumaric acid, and maleic acid, and (iii) salts with sulfonic acids such as methanesulfonic acid, benzenesulfonic acid, p-toluenesulfonic acid, mesitylenesulfonic acid, naphthalenesulfonic acid, and the like.

In the morphinan derivatives represented by the above formula (I), a tautomer or a stereoisomer of the compound, a pharmaceutically acceptable salt thereof or a solvate thereof, examples of stereoisomers include a cis and trans isomers, a racemate, an optically active substance.

In the morphinan derivative represented by the above formula (I), a tautomer or a stereoisomer of the compound, a pharmaceutically acceptable salt thereof or a solvate thereof, these may also exist as a hydrate or a solvate. Accordingly, the compound according to the present invention includes all crystalline forms and hydrates or solvates thereof.

Next, a method of preparing the morphinan derivative represented by the above formula (I), a tautomer or a stereoisomer of the compound, a pharmaceutically acceptable salt thereof or a solvate thereof is shown below.

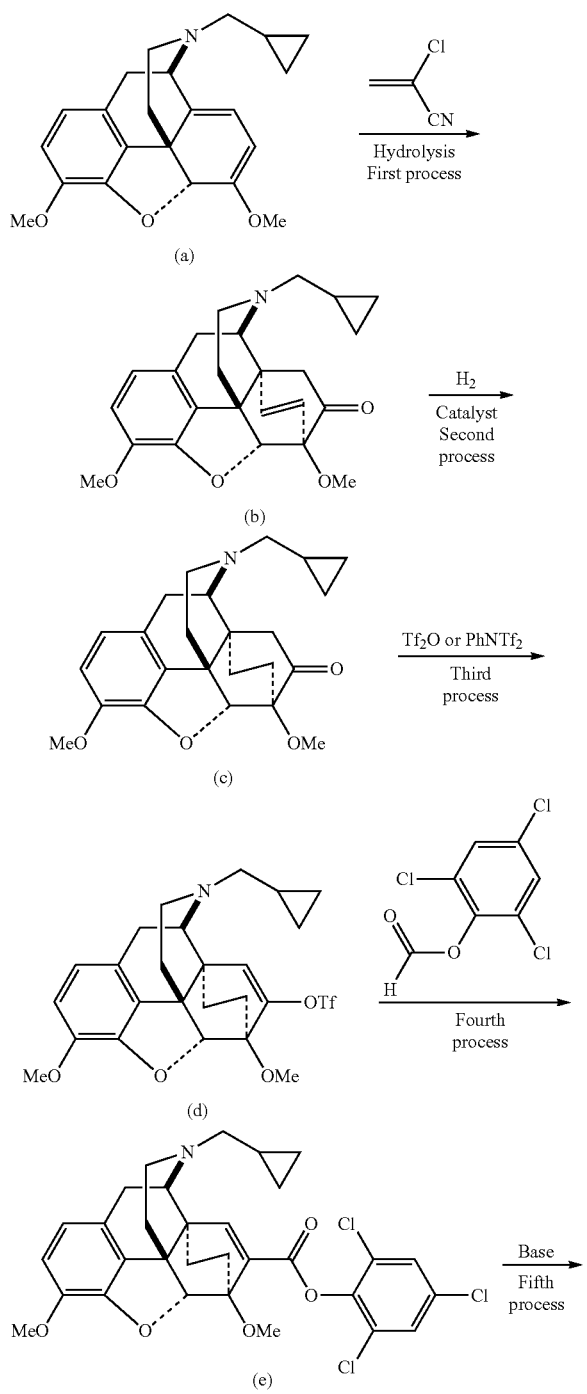

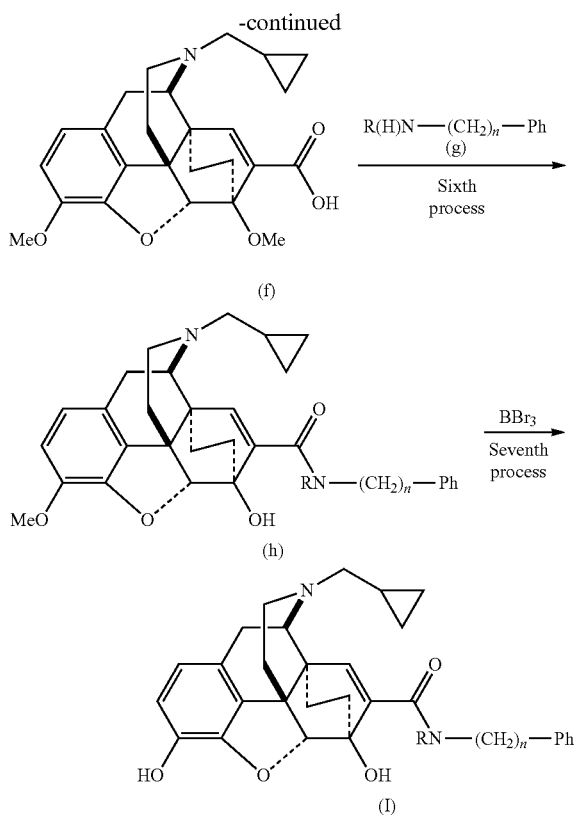

(wherein R and n are the same as defined above)

(First Process)

A raw material (a) is reacted with 2-chloroacrylonitrile in a solvent such as an aromatic hydrocarbon (e.g., benzene, toluene or xylene), an ether (e.g., diethyl ether, tetrahydrofuran, dioxane, monoglyme or diglyme), an alcohol (e.g., methanol or ethanol), an aliphatic hydrocarbon (e.g., pentane, hexane, heptane or ligroin) or an aprotic polar solvent (e.g., dimethylformamide or dimethylsulfoxide), at 80 to 190° C. for 3 to 24 hours or irradiating microwaves by a microwave synthesizer to perform a reaction in a sealed tube, followed by hydrolysis to synthesize a compound (b). The hydrolysis reaction may be performed using any known acid or base, and a base is preferred. For example, the hydrolysis reaction may be performed by adding a 1 to 10 mol/l inorganic base aqueous solution such as a lithium hydroxide, sodium hydroxide, or potassium hydroxide aqueous solution in an amount of from 1 to 5 equivalents in a solvent such as an ether (e.g., tetrahydrofuran or dioxane) or an alcohol solvent (e.g., methanol or ethanol), and reacting by heating under reflux for 1 to 24 hours.

A starting material (a) may be synthesized using a generally known method. For example, it may be synthesized using methods described in J. Chem. Soc. C, 1966, 617, J. Chem. Soc. C, 1969, 2569 and J. Chem. Soc. Perkin Trans. I, 1994, 911.

(Second Process)

In a hydrogen atmosphere, a compound (b) is reacted in a solvent such as an ether (e.g., diethyl ether, tetrahydrofuran, dioxane, monoglyme or diglyme) or an alcohol (e.g., methanol or ethanol) in the presence of a metal catalyst such as nickel (Raney nickel or the like), palladium (palladium-activated carbon (Pd/C)), Pearlman's catalyst (Pd(OH)$_2$ or the like), platinum (Adams catalyst (PtO$_2$) or the like) at a temperature from room temperature to reflux temperature for 1 to 24 hours, so as to synthesize a compound (c).

(Third Process)

In an inert gas atmosphere, the compound (c) is reacted with trifluoromethanesulfonic anhydride or N-phenyl-bis (trifluoromethanesulfonimide) in a solvent such as an ether (e.g., diethyl ether, tetrahydrofuran, dioxane, monoglyme or diglyme) or a halogenated hydrocarbon (e.g., methylene chloride, chloroform or carbon tetrachloride) in the presence of a base (e.g., potassium bis(trimethylsilyl)amide (KHMDS) or lithium diisopropylamide (LDA)), an organic base (e.g., trimethylamine, triethylamine, tributylamine, pyridine, N,N-dimethylaniline, N,N-dimethylaminopyridine, N-methylpiperidine, N-methylmorpholine, diethylamine, cyclohexylamine or procaine) or an inorganic base (e.g., potassium carbonate or lithium carbonate) at a temperature ranging from −78° C. to room temperature for 30 minutes to 5 hours, so as to synthesize a compound (d).

(Fourth Process)

In an inert gas atmosphere, the compound (d) is reacted with 2,4,6-trichlorophenyl formate in a solvent such as an ether (e.g., diethyl ether, tetrahydrofuran, dioxane, monoglyme or diglyme) or an aromatic hydrocarbon (e.g., benzene, toluene or xylene) in the presence of a zero-valent palladium catalyst (e.g., tetrakis(triphenylphosphine)palladium, or a divalent palladium catalyst (e.g., palladium acetate or dichlorobis(tri-o-tolylphosphine)palladium and a phosphine ligand (e.g., Xantphos, DPEPhos or (±)-BINAP) and an organic base (e.g., trimethylamine, triethylamine, tributylamine, pyridine, N,N-dimethylaniline, N-methylpiperidine, N-methylmorpholine, diethylamine, cyclohexylamine or procaine) or an inorganic base (e.g., potassium carbonate or lithium carbonate) at a temperature from 0° C. to reflux temperature for 1 to 24 hours, so as to synthesize a compound (e).

(Fifth Process)

The compound (e) is hydrolyzed in a solvent such as water, an alcohol (e.g., methanol, ethanol or propanol), an ether (e.g., tetrahydrofuran or dioxane), a ketone (e.g., acetone or methyl ethyl ketone), acetic acid, or a mixed solvent thereof in the presence of a base (e.g., lithium hydroxide, sodium hydroxide, potassium hydroxide, sodium carbonate or potassium carbonate), a mineral acid (e.g., hydrochloric acid, sulfuric acid or hydrobromic acid) or an organic acid (e.g., p-toluenesulfonic acid) at a temperature of room temperature to 120° C. for 1 to 24 hours, so as to synthesize a compound (0).

(Sixth Process)

The compound (f) is reacted with an amine (g) using a condensing agent such as O-(7-azabenzotriazol-1-yl)-N,N, N',N'-tetramethyluronium hexafluorophosphate (HATU), O-(benzotriazol-1-yl)-N,N, N',N'-tetramethyluronium hexafluorophosphate (HBTU), N,N'-dicyclohexylcarbodiimide (DCC), 1-ethyl-3-(3-dimethylaminopropyl)carbodiimide hydrochloride (WSC), 4-(4,6-dimethoxy-1,3,5-triazin-2-yl)-4-methylmorpholinium chloride n hydrate (DMT-MM), and the like in a solvent such as an aromatic hydrocarbon (e.g., benzene, toluene or xylene), an ether (e.g., diethyl ether, tetrahydrofuran, dioxane, monoglyme or diglyme), a halogenated hydrocarbon (methylene chloride, chloroform or carbon tetrachloride), an alcohol (methanol or ethanol), an aliphatic hydrocarbon (e.g., pentane, hexane, heptane or ligroin) or an aprotic polar solvent (e.g., dimethylformamide or dimethylsulfoxide) in the presence of an organic base (e.g., N,N-dimethylaminopyridine, trimethylamine, triethylamine, tributylamine, N,N-diisopropylethylamine, pyridine, N,N-dimethylaniline, N-methylpiperidine, N-methylmorpholine, diethylamine, cyclohexylamine or procaine) or an inorganic base (e.g., potassium carbonate or lithium carbonate) at a temperature of 0° C. to reflux temperature for 1 to 12 hours, so as to synthesize a compound (h).

Alternatively, the compound (h) may be directly synthesized from the following compound (e).

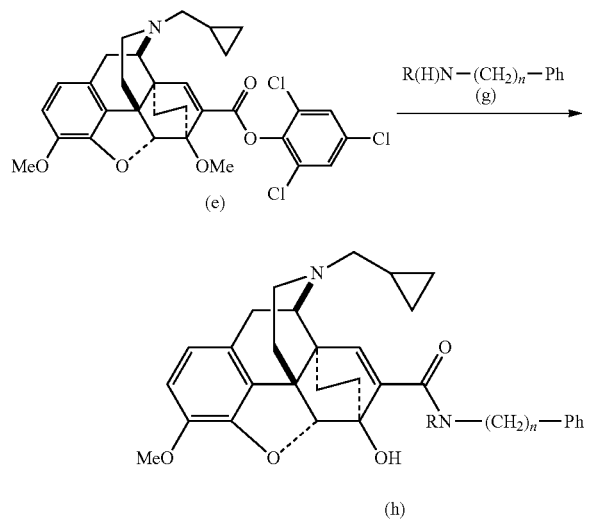

The compound (e) is reacted with an amine (g) in a solvent such as an ether (e.g., diethyl ether, tetrahydrofuran, dioxane, monoglyme or diglyme) in the presence of an organic base (e.g., N,N-dimethylaminopyridine, trimethylamine, triethylamine, tributylamine, pyridine, N,N-dimethylaniline, N-methylpiperidine, N-methylmorpholine, diethylamine, cyclohexylamine or procaine) or an inorganic base (e.g., potassium carbonate or lithium carbonate) at a temperature of 0° C. to reflux for 1 to 12 hours, so as to synthesize a compound (h).

(Seventh Process)

The compound (h) is reacted with boron tribromide in a solvent such as a halogenated hydrocarbon (e.g., methylene chloride, chloroform or carbon tetrachloride) at a temperature of −30° C. to 50° C. for 30 minutes to 5 hours, so as to obtain a compound (I).

The compound obtained by (First process) to (Seventh process) may be purified by, for example, silica gel column chromatography if necessary. Further, an acid addition salt may be formed by a conventional method if necessary, for example, this may be performed at room temperature or by suitably heating the compound (I) according to the present invention in a solvent such as organic solvents such as ethyl acetate; alcohols such as methanol, ethanol, and the like; or polar solvents such as water in the presence of mineral acids such as hydrochloric acid, sulfuric acid, phosphoric acid, and the like, organic carboxylic acids such as formic acid, acetic acid, citric acid, trichloroacetic acid, trifluoroacetic acid, fumaric acid, maleic acid, and the like, and organic sulfonic acids such as methanesulfonic acid, benzenesulfonic acid, p-toluenesulfonic acid, mesitylenesulfonic acid, and naphthalenesulfonic acid.

Next, the results of pharmacological tests will be described.

It was determined that the compound according to the present invention showed a strong affinity for the opioid κ receptor by Test Example 1, showed a potent agonistic activity for the opioid κ receptor by Test Example 2, showed potent analgesic effects by Test Example 3 and did not show a sedative effect as compared with existing drugs by Test Example 4. Moreover, the compound according to the present invention has already been confirmed not to have drug aversive effects.

Examples of diseases and symptoms associated with the opioid κ receptor include cardiovascular disorders, digestive system diseases, blood system diseases, respiratory diseases, liver diseases, nervous system disorders, urinary system disorders, pain, cough, pruritus, ischemic brain diseases, and drug dependence.

Accordingly, the morphinan derivatives represented by the above formula (I), a tautomer or a stereoisomer of the compound, a pharmaceutically acceptable salt thereof or a solvate thereof have high opioid κ receptor-selectivity and potent agonistic activity for the opioid κ receptor, and thus are effective for the treatment, amelioration and prevention of these diseases and symptoms.

Further, the morphinan derivatives represented by the above formula (I), a tautomer or a stereoisomer of the compound, a pharmaceutically acceptable salt thereof or a solvate thereof may be formulated into a composition together with a pharmaceutically acceptable carrier to be administered to a human by parenteral administration, oral administration in solid or liquid form, etc. Further, they may be used with other analgesics and antipruritic drugs according to the application.

Examples of solid formulations for oral administration include capsules, tablets, pills, powders, granules, etc. In preparing this solid formulation, excipients, disintegrating agents, binders, lubricants, dyes, and the like may be used. Here, examples of the excipients include lactose, D-mannitol, crystalline cellulose, glucose, and the like, examples of the disintegrating agents include starch, carboxymethylcellulose calcium (CMC-Ca), and the like, examples of the lubricants include magnesium stearate, talc, and the like, and examples of the binders include hydroxypropylcellulose (HPC), gelatin, polyvinylpyrrolidone (PVP), and the like. In the case of capsules, tablets and pills, a buffer agent may be further used. For tablets and pills, an enteric coating may be applied.

Aspects of the composition according to the present invention for injection include pharmaceutically acceptable sterile water or nonaqueous solutions, suspensions or emulsions. Examples of a suitable non-aqueous carrier, diluting agent, solvent or vehicle include propylene glycol, polyethylene glycol, vegetable oils such as olive oil and injectable organic esters such as ethyl oleate. Such a composition may contain auxiliary agents such as an antiseptic agent, a wetting agent, an emulsifier, a soothing agent, a buffering agent, a preservative and a dispersant.

These compositions may be sterilized by, for example, filtration with a bacteria-retaining filter, or by incorporating therein a sterilizing agent in a form of a sterile solid composition or by being dissolved in a sterilizing agent or some other medium which can be used for a sterilized injection immediately before use.

For formulation for ophthalmic administration, solubilizers, preservatives, isotonicity agents, thickeners, and the like may be added in addition to the compound according to the present invention.

Examples of the liquid formulation for oral administration include a pharmaceutically acceptable emulsion, solution, suspension, syrup and elixir which contain an inert diluting agent commonly used by those skilled in the art, for example, water. In addition to inert diluting agents, the composition may be formulated with auxiliary agents such as a wetting agent, emulsifier, suspension, sweetener, seasoning agent and flavoring agent.

In the case of formulation for rectal administration, an excipient such as cacao butter and suppository wax are preferably included in addition to the compound according to the present invention.

As for the dose of the morphinan derivatives represented by the above formula (I), a tautomer or a stereoisomer of the compound, a pharmaceutically acceptable salt thereof or a solvate thereof, in terms of an active ingredient, administration to adults is usually at a dose of 0.01 μg to 1 g/day, preferably 0.0001 to 200 mg/day, in the case of injection, or a dose of 0.1 μg to 10 g/day, and preferably 0.001 to 2000 mg/day, in the case of oral administration, but the dose may be reduced or increased depending on age, symptoms, and the like. Alternatively, this daily dose may be administered separately in 2 to 4 portions as desired.

EXAMPLES

Hereafter, the present invention will be further explained in more detail with reference to reference examples, examples and test examples. However, the present invention is not limited to these examples.

Reference Example 1

Synthesis of (4R,4aR,7S,7aR,12bS)-3-(cyclopropyl-methyl)-7,9-dimethoxy-1,2,3,4,7,7a-hexahydro-4a, 7-ethano-4,12-methanobenzofuro[3,2-e]isoquinolin-14-one (1)

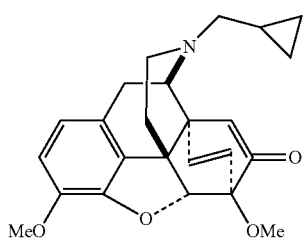

1

Three vials for microwave reaction in which a 1,2-dichloroethane solution (10 mL) of (4R,7aR,12bS)-3-(cyclopropylmethyl)-7,9-dimethoxy-2,3,4,7a-tetrahydro-1H-4,12-methanobenzofuro[3,2-e]isoquinoline (synthesized using a method described in J. Chem. Soc. C, 1966, 617, J. Chem. Soc. C, 1969, 2569 and J. Chem. Soc. Perkin Trans. I, 1994, 911) (2.0 g, 5.63 mmol) was introduced and then 2-chloroacrylonitrile (4.5 mL, 56.6 mmol) was added thereto were scaled and prepared. Each vial was irradiated with microwaves in a microwave synthesizer and reacted for 30 minutes under conditions of 180° C. and 10 bar. After cooling, the contents of the three vials were combined and concentrated under reduced pressure. The residue was purified by silica gel column chromatography (25 to 50% ethyl acetate/hexane). The resulting 2-chloroacrylonitrile adduct was dissolved in ethanol (144 mL), a 1 M aqueous sodium hydroxide solution (36 mL) was added thereto and the mixture was refluxed for 3 hours. After cooling, water (200 mL) was added thereto and the mixture was extracted twice with diethyl ether. The combined organic layers were washed with brine twice, dried over magnesium sulfate and concentrated under reduced pressure. The resulting crude material was purified by silica gel column chromatography (25 to 50% ethyl acetate/hexane), and a title compound 1 (2.5 g, 44%) was obtained as a colorless amorphous substance.

$^1$H-NMR (400 MHz, CDCl$_3$) δ (ppm): 0.08-0.20 (m, 2H), 0.45-0.60 (m, 2H), 0.77-0.91 (m, 1H), 1.87 (dd, J=2.8, 12.8 Hz, 1H), 2.07 (ddd, J=5.4, 12.8, 12.8 Hz, 1H), 2.17 (d, J=18.8 Hz, 1H), 2.32-2.55 (m, 4H), 2.77 (dd, J=5.4, 11.9 Hz, 1H), 3.17 (d, J=18.3 Hz, 1H), 3.32 (d, J=18.8 Hz, 1H), 3.63 (s, 3H), 3.65 (d, J=6.9 Hz, 1H), 3.83 (s, 3H), 4.68 (d, J=1.4 Hz, 1H), 5.70 (d, J=8.7 Hz, 1H), 5.88-5.93 (m, 1H), 6.57 (d, J=7.8 Hz, 1H), 6.66 (d, J=7.8 Hz, 1H).

Reference Example 2

Synthesis of (4R,4aS,7S,7aR,12bS)-3-(cyclopropyl-methyl)-7,9-dimethoxy-1,2,3,4,7,7a-hexahydro-4a, 7-ethano-4,12-methanobenzofuro[3,2-e]isoquinolin-6(5H)-one (2)

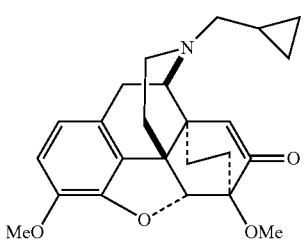

2

Compound 1 (2.43 g, 6.18 mmol) was dissolved in ethanol (100 mL) and 5% palladium-activated carbon (2.01 g) was added thereto. The mixture was stirred in a hydrogen atmosphere at 60° C. for 12 hours, was allowed to cool, and filtered through a celite pad. The filtrate was concentrated under reduced pressure, a saturated sodium hydrogen carbonate aqueous solution (100 mL) was added to the residue, and the mixture was extracted twice with chloroform. The combined organic layers were dried over sodium sulfate and concentrated under reduced pressure. The residue was dissolved in methanol, filtered and purified by recrystallization, and a title compound 2 (2.25 g, 92%) was obtained as colorless plate crystal (melting point: 164 to 165° C.).

$^1$H-NMR (400 MHz, CDCl$_3$) δ (ppm): 0.06-0.16 (m, 2H), 0.43-0.56 (m, 2H), 0.73-0.86 (m, 1H), 1.01 (dddd, J=3.2, 3.2, 12.8, 12.8 Hz, 1H), 1.26 (ddd, J=6.0, 12.8, 12.8 Hz, 1H), 1.49-1.61 (m, 1H), 1.68 (dd, J=3.7, 13.3 Hz, 1H), 1.76 (ddd, J=6.0, 12.8, 12.8 Hz, 1H), 2.01 (ddd, J=5.8, 12.8, 12.8 Hz, 1H), 2.22 (d, J=19.7 Hz, 1H), 2.29-2.42 (m, 4H), 2.70 (dd, J=5.8, 11.9 Hz, 1H), 3.07 (d, J=18.3 Hz, 1H), 3.13 (d, J=6.4 Hz, 1H), 3.46-3.55 (m, 1H), 3.53 (s, 3H), 3.89 (s, 3H), 4.60 (s, 1H), 6.63 (d, J=8.2 Hz, 1H), 6.76 (d, J=8.2 Hz, 1H).

Reference Example 3

Synthesis of (4R,4aS,7S,7aR,12bS)-3-(cyclopropylmethyl)-7,9-dimethoxy-1,2,3,4,7,7a-hexahydro-4a,7-ethano-4,12-methanobenzofuro[3,2-e]isoquinolin-6-yl trifluoromethanesulfonate (3)

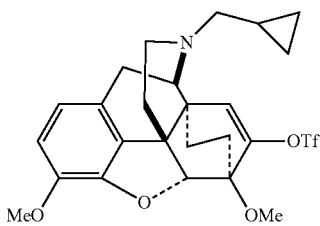

In an argon atmosphere, a 11% KHMDS toluene solution (5.5 mL, 2.75 mmol) was added to anhydrous THF (4 mL) and the mixture was cooled to −78° C. A solution of Compound 2 (885 mg, 2.24 mmol) in anhydrous THF (4 mL) and a solution of N-phenyl-bis(trifluoromethanesulfonimide) (1.1 g, 3.36 mmol) in anhydrous THF (2 mL) were sequentially added, and the mixture was stirred for 1 hour. A saturated sodium hydrogen carbonate aqueous solution (5 mL) was added thereto and the temperature was raised to room temperature. A saturated sodium hydrogen carbonate aqueous solution (30 mL) was added to the reaction mixture and the mixture was extracted twice with ethyl acetate. The combined organic layers were dried over sodium sulfate and concentrated under reduced pressure. The resulting crude material was purified by silica gel column chromatography (15 to 25% diethyl ether/hexane), and a title compound 3 (1.17 g, 99%) was obtained as a colorless oil material.

$^1$H-NMR (400 MHz, CDCl$_3$) δ (ppm): 0.08-0.20 (m, 2H), 0.46-0.61 (m, 2H), 0.76 (ddd, J=2.8, 9.6, 12.8 Hz, 1H), 0.80-0.92 (m, 1H), 1.03 (ddd, J=5.6, 12.4, 12.4 Hz, 1H), 1.43 (dddd, J=2.4, 2.4, 12.4, 12.4 Hz, 1H), 1.65 (dd, J=2.4, 13.3 Hz, 1H), 1.79 (ddd, J=5.6, 9.6, 12.4 Hz, 1H), 1.91 (ddd, J=5.6, 12.8, 12.8 Hz, 1H), 2.26-2.45 (m, 4H), 2.62 (dd, J=5.6, 12.0 Hz, 1H), 3.09 (d, J=18.3 Hz, 1H), 3.42 (d, J=6.4 Hz, 1H), 3.58 (s, 3H), 3.90 (s, 3H), 4.62 (d, J=2.4 Hz, 1H), 6.54 (s, 1H), 6.61 (d, J=8.2 Hz, 1H), 6.76 (d, J=8.2 Hz, 1H).

Reference Example 4

Synthesis of 2,4,6-trichlorophenyl(4R,4aS,7R,7aR 12bS)-3-(cyclopropylmethyl)-7,9-dimethoxy-1,2,3,4,7,7a-hexahydro-4a,7-ethano-4,12-methanobenzofuro[3,2-e]isoquinoline-6-carboxylate (4)

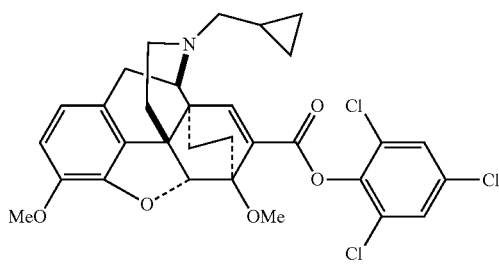

Compound 3 (1.07 g, 2.03 mmol) was dissolved in toluene (15 mL), and 2,4,6-trichlorophenyl formate (564 mg, 2.50 mmol), palladium acetate (46 mg, 0.205 mmol) and 4,5-bis(diphenylphosphino)-9,9-dimethyxanthene (234 mg, 404 mmol) were added thereto. Triethylamine (0.34 mL) was slowly added dropwise in an argon atmosphere, and the mixture was stirred at room temperature for 10 hours. A saturated sodium hydrogen carbonate aqueous solution (15 mL) was added and the mixture was extracted three times with ethyl acetate. The combined organic layers were dried over sodium sulfate and concentrated under reduced pressure. The resulting crude material was purified by silica gel column chromatography (ethyl acetate:hexane=1:6), and a title compound 4 (1.1 g, 90%) was obtained as a colorless amorphous substance.

$^1$H-NMR (400 MHz, CDCl$_3$) δ (ppm): 0.09-0.21 (m, 2H), 0.47-0.62 (m, 2H), 0.74-0.84 (m, 1H), 0.85-0.96 (m, 1H), 0.98 (ddd, J=5.5, 12.8, 12.8 Hz, 1H), 1.43-1.54 (m, 1H), 1.66-1.76 (m, 2H), 1.81 (ddd, J=5.5, 12.8, 12.8 Hz, 1H), 2.28-2.51 (m, 4H), 2.63 (dd, J=4.6, 11.9 Hz, 1H), 3.12 (d, J=18.3 Hz, 1H), 3.51 (d, J=6.9 Hz, 1H), 3.56 (s, 3H), 3.90 (s, 3H), 4.65 (d, J=1.4 Hz, 1H), 6.63 (d, J=8.0 Hz, 1H), 6.77 (d, J=8.0 Hz, 1H), 7.40 (s, 2H), 8.07 (s, 1H).

Reference Example 5

Synthesis of (4R,4aS,7R,7aR,12bS)-3-(cyclopropylmethyl)-7,9-dimethoxy-1,2,3,4,7,7a-hexahydro-4a,7-ethano-4,12-methanobenzofuro[3,2-e]isoquinoline-6-carboxylic acid hydrochloride (5)

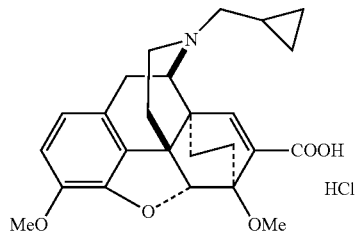

Compound 4 (54.9 mg, 0.0909 mmol) was dissolved in THF (2 mL), and a 1 M aqueous sodium hydroxide solution (2 mL) was added thereto and the mixture was stirred at 60° C. After 7 hours, a 6 M aqueous sodium hydroxide solution (1 mL) was added and the mixture was stirred at 60° C. for 3 hours. After cooling, a saturated ammonium chloride aqueous solution (10 mL) was added thereto and the mixture was extracted three times with 2-propanol/chloroform (1:4). The combined organic layers were dried over sodium sulfate and concentrated under reduced pressure. The resulting crude material was dissolved in methanol (3 mL), a 1 M hydrogen chloride-ethyl acetate solution (0.3 mL, 0.300 mmol) was added thereto and the mixture was stirred. After diethyl ether (50 mL) was added little by little, the mixture was allowed to stand while cooling with ice for 30 minutes, the precipitated white precipitate was collected by filtration, and a title compound 5 (25 mg, 60%) which was a white solid (melting point: 137 to 138° C.) was obtained.

$^1$H-NMR (400 MHz, CD$_3$OD) δ (ppm): 0.47-0.64 (m, 2H), 0.75-0.94 (m, 3H), 1.11-1.30 (m, 2H), 1.34-1.46 (m, 1H), 1.61-1.73 (m, 1H), 1.93-2.17 (m, 2H), 3.03 (dd, J=6.9, 19.7 Hz, 1H), 3.08-3.24 (m, 2H), 3.29-3.53 (m, 3H), 3.56 (s, 3H), 3.89 (s, 3H), 4.50 (d, J=6.9 Hz, 1H), 4.67 (d, J=1.1 Hz, 1H), 6.81 (d, J=8.2 Hz, 1H), 6.95 (d, J=8.2 Hz, 1H), 7.71 (s, 1H).

Reference Example 6

Synthesis of (4R,4aS,7R,7aR,12bS)-3-(cyclopropylmethyl)-7,9-dimethoxy-N-phenyl-1,2,3,4,7,7a-hexahydro-4a,7-ethano-4,12-methanobenzofuro[3,2-e]isoquinoline-6-carboxamide (6)

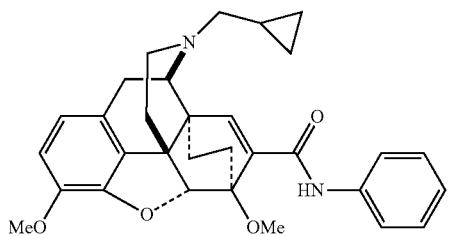

6

Compound 5 (45 mg, 0.0978 mmol) was suspended in dichloromethane (4 mL). Then, N,N-diisopropylethylamine (50 μL, 0.280 mmol), aniline (10 μL, 0.110 mmol) and O-(7-azabenzotriazol-1-yl)-N,N,N',N'-tetramethyluronium hexafluorophosphate (HATU) (39 mg, 0.110 mmol) were added thereto and the mixture was stirred at room temperature for 1 hour. After the reaction mixture was concentrated under reduced pressure, the residue was purified by silica gel column chromatography (40 to 60% ethyl acetate/hexane), and a title compound 6 (47 mg, 96%) was obtained as a colorless amorphous substance.

$^1$H-NMR (400 MHz, CDCl$_3$) δ (ppm): 0.08-0.19 (m, 2H), 0.45-0.59 (m, 2H), 0.71-0.80 (m, 1H), 0.87-1.01 (m, 2H), 1.27-1.38 (m, 1H), 1.61 (dd, J=2.3, 12.8 Hz, 1H), 1.82 (dddd, J=5.2, 12.8, 12.8 Hz, 1H), 1.91 (ddd, J=5.2, 9.9, 12.1 Hz, 1H), 2.27-2.43 (m, 4H), 2.60 (dd, J=5.2, 11.9 Hz, 1H), 3.10 (d, J=18.3 Hz, 1H), 3.48 (d, J=6.4 Hz, 1H), 3.72 (s, 3H), 3.91 (s, 3H), 4.55 (d, J=2.3 Hz, 1H), 6.63 (d, J=8.0 Hz, 1H), 6.77 (d, J=8.0 Hz, 1H), 7.10 (dd, J=7.8, 7.8 Hz, 1H), 7.34 (dd, J=7.8, 7.8 Hz, 2H), 7.64 (d, J=7.8 Hz, 2H), 7.97 (s, 1H), 9.91 (s, 1H).

Reference Example 7

Synthesis of (4R,4aS,7R,7aR,12bS)-N-benzyl-3-(cyclopropylmethyl)-7,9-dimethoxy-1,2,3,4,7,7a-hexahydro-4a,7-ethano-4,12-methanobenzofuro[3,2-e]isoquinoline-6-carboxamide (7)

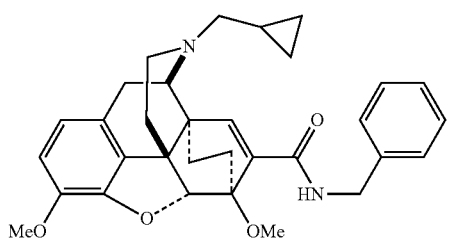

7

Compound 4 (31.7 mg, 0.0525 mmol) was dissolved in THF (2 mL). Then, benzylamine (13 μL, 0.119 mmol), triethylamine (19 μL, 0.136 mmol) and N,N-dimethyl-4-aminopyridine (1.0 mg, 0.0082 mmol) were added thereto and the mixture was stirred at 50° C. for 2.5 hours. The reaction mixture was concentrated under reduced pressure, and the residue was purified by preparative thin layer chromatography (28% aqueous ammonia:methanol:chloroform=1:9:400). A title compound 7 (20 mg, 74%) was obtained as a colorless oil material.

$^1$H-NMR (400 MHz, CDCl$_3$) δ (ppm): 0.08-0.18 (m, 2H), 0.46-0.58 (m, 2H), 0.67-0.77 (m, 1H), 0.85-0.98 (m, 2H), 1.26 (dddd, J=2.3, 2.3, 11.9, 11.9 Hz, 1H), 1.59 (dd, J=2.3, 12.8 Hz, 1H), 1.72-1.90 (m, 2H), 2.25-2.44 (m, 4H), 2.60 (dd, J=5.0, 11.9 Hz, 1H), 3.08 (d, J=18.3 Hz, 1H), 3.46 (d, J=6.4 Hz, 1H), 3.49 (s, 3H), 3.89 (s, 3H), 4.47 (d, J=2.3 Hz, 1H), 4.53 (dd, J=5.5, 14.7 Hz, 1H), 4.60 (dd, J=5.5, 14.7 Hz, 1H), 6.61 (d, J=8.0 Hz, 1H), 6.75 (d, J=8.0 Hz, 1H), 7.25-7.39 (m, 5H), 7.85 (s, 1H), 8.12 (br t, J=5.5 Hz, 1H).

Reference Example 8

Synthesis of (4R,4aS,7R,7aR,12bS)-3-(cyclopropylmethyl)-7,9-dimethoxy-N-phenethyl-1,2,3,4,7,7a-hexahydro-4a,7-ethano-4,12-methanobenzofuro[3,2-e]isoquinoline-6-carboxamide (8)

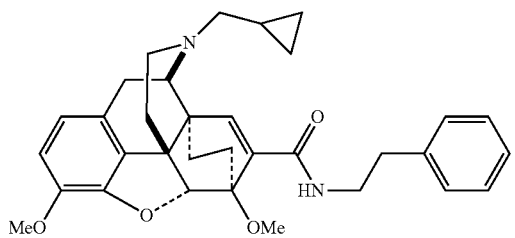

8

Compound 4 (135.7 mg, 0.225 mmol) was dissolved in THF (4 mL), and then triethylamine (63 μL, 0.452 mmol), phenethylamine (46 μL, 0.365 mmol) and N,N-dimethyl-4-aminopyridine (2.8 mg, 0.0229 mmol) were added thereto and the mixture was stirred at 50° C. for 3.5 hours. The reaction mixture was concentrated under reduced pressure and the residue was purified by silica gel column chromatography (50 to 70% ethyl acetate/hexane), and a title compound 8 (108 mg, 91%) was obtained as a colorless oil material.

$^1$H-NMR (400 MHz, CDCl$_3$) δ (ppm): 0.08-0.17 (m, 2H), 0.45-0.57 (m, 2H), 0.64-0.74 (m, 1H), 0.83-0.95 (m, 2H), 1.18 (dddd, J=2.3, 2.3, 12.4, 12.4 Hz, 1H), 1.56 (dd, J=2.3, 13.1 Hz, 1H), 1.71-1.85 (m, 2H), 2.23-2.41 (m, 4H), 2.57 (dd, J=5.0, 11.9 Hz, 1H), 2.89 (t, J=6.9 Hz, 2H), 3.06 (d, J=18.3 Hz, 1H), 3.35 (s, 3H), 3.43 (d, J=6.9 Hz, 1H), 3.61-3.69 (m, 2H) 3.88 (s, 3H), 4.39 (d, J=2.3 Hz, 1H), 6.60 (d, J=8.0 Hz, 1H), 6.77 (d, J=8.0 Hz, 1H), 7.18-7.35 (m, 5H), 7.80 (s, 1H), 7.85 (br t, J=5.0 Hz, 1H).

Reference Example 9

Synthesis of (4R,4aS,7R,7aR,12bS)-N-benzyl-3-(cyclopropylmethyl)-7,9-dimethoxy-N-methyl-1,2,3,4,7,7a-hexahydro-4a,7-ethano-4,12-methanobenzofuro[3,2-e]isoquinoline-6-carboxamide (9)

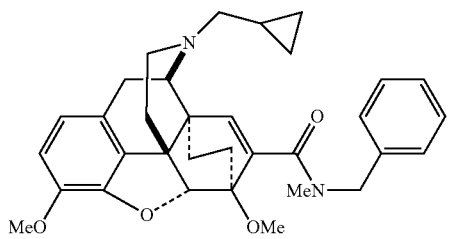

A compound 4 (24.5 mg, 0.0406 mmol) was dissolved in THF (2 mL), and then triethylamine (13 μL, 0.0933 mmol), benzylmethylamine (26 μL, 0.202 mmol) and N,N-dimethyl-4-aminopyridine (1.3 mg, 0.0106 mmol) were added thereto, and the mixture was stirred at 50° C. for 3.5 hours. The reaction mixture was concentrated under reduced pressure and the residue was purified by preparative thin layer chromatography (28% aqueous ammonia:methanol:chloroform=1:9:200). A title compound 9 (18.3 mg, 86%) was obtained as a colorless oil material.

$^1$H-NMR (400 MHz, CDCl$_3$) δ (ppm): 0.06-0.19 (m, 2H), 0.44-0.60 (m, 2H), 0.65-0.94 (m, 2.4H), 1.00 (ddd, J=5.5, 12.4, 12.4 Hz, 0.6H), 1.30-1.43 (m, 0.4H), 1.55-1.76 (m, 2H), 1.81-2.03 (m, 1.6H), 2.23-2.46 (m, 4H), 2.47-2.66 (m, 1H), 2.92 (s, 1.2H), 2.95 (s, 1.8H), 3.05 (d, J=18.3 Hz, 0.4H), 3.09 (d, J=18.3 Hz, 0.6H), 3.31 (d, J=5.5 Hz, 0.4H), 3.43 (d, J=5.5 Hz, 0.6H), 3.54 (s, 1.8H), 3.59 (s, 1.2H), 3.89 (s, 1.2H), 3.90 (s, 1.8H), 4.48-4.91 (m, 3H), 6.58 (d, J=8.4 Hz, 0.4H), 6.60 (d, J=8.0 Hz, 0.6H), 6.66-6.72 (m, 1H), 6.73 (d, J=8.0 Hz, 0.4H), 6.75 (d, J=8.0 Hz, 0.6H), 7.24-7.41 (m, 5H).

Example 1

Synthesis of (4R,4aS,7R,7aR,12bS)-3-(cyclopropylmethyl)-7,9-dihydroxy-N-phenyl-1,2,3,4,7,7a-hexahydro-4a,7-ethano-4,12-methanobenzofuro[3,2-e]isoquinoline-6-carboxamide hydrochloride (10)

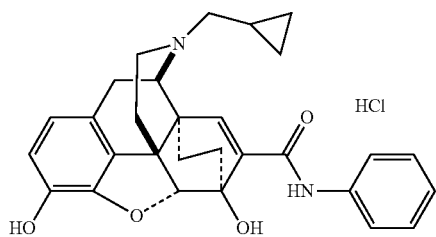

A compound 6 (26.3 mg, 0.0527 mmol) was dissolved in dichloromethane (2 mL), and a 1.0 M boron tribromide dichloromethane solution (0.26 mL, 0.260 mmol) was added thereto under ice cooling, and the mixture was stirred at room temperature for 50 minutes. 28% aqueous ammonia (1.5 mL) was added thereto under ice cooling, and the mixture was further stirred at room temperature for 10 hours. A saturated sodium hydrogen carbonate aqueous solution (6 mL) was added thereto and the mixture was extracted three times with chloroform. The combined organic layers were dried over sodium sulfate and concentrated under reduced pressure. The residue was purified by silica gel column chromatography (0 to 3% methanol/chloroform), and a free form of a title compound 10 (23.5 mg, 95%) was obtained as a colorless amorphous substance. The free form was dissolved in ethyl acetate (2 mL) and a 1 M hydrogen chloride-ethyl acetate solution (0.2 mL, 0.200 mmol) was added thereto. Diethyl ether (4 mL) was added thereto and the mixture was stirred under ice-cooling for 30 minutes, the resulting white precipitate was collected by filtration, and thereby a title compound 10 was obtained.

(Free Form)
$^1$H-NMR (400 MHz, CDCl$_3$) δ (ppm): 0.07-0.20 (m, 2H), 0.44-0.59 (m, 2H), 0.62-0.73 (m, 1H), 0.79-0.96 (m, 2H), 1.22-1.37 (m, 1H), 1.54-1.73 (m, 2H), 1.79 (ddd, J=5.0, 12.8, 12.8 Hz, 1H), 2.22-2.39 (m, 3H), 2.43 (dd, J=6.0, 12.4 Hz, 1H), 2.59 (dd, J=5.0, 11.7 Hz, 1H), 3.06 (d, J=18.3 Hz, 1H), 3.48 (d, J=6.4 Hz, 1H), 4.43 (s, 1H), 5.71 (br s, 1H), 6.56 (d, J=8.2 Hz, 1H), 6.77 (d, J=8.2 Hz, 1H), 7.05-7.13 (m, 1H), 7.25-7.34 (m, 2H), 7.58 (d, J=8.0 Hz, d, 1H), 7.58 (d, J=8.0 Hz, 1H), 7.77 (s, 1H), 9.35-9.52 (m, 1H).

Example 2

Synthesis of (4R,4aS,7R,7aR,12bS)-N-benzyl-3-(cyclopropylmethyl)-7,9-dihydroxy-1,2,3,4,7,7a-hexahydro-4a,7-ethano-4,12-methanobenzofuro[3,2-e]isoquinoline-6-carboxamide hydrochloride (16)

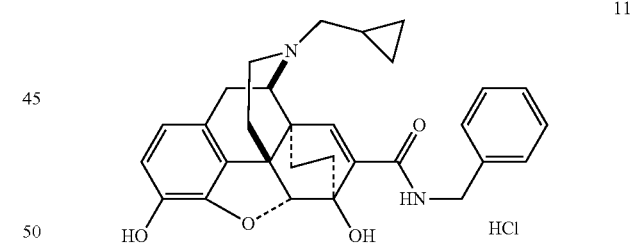

A compound 7 (20 mg, 0.039 mmol) was dissolved in dichloromethane (1 mL), and then a 1.0 M boron tribromide dichloromethane solution (0.2 mL, 0.200 mmol) was added thereto under ice cooling, and the mixture was stirred at room temperature for 30 minutes. A saturated sodium hydrogen carbonate aqueous solution (4 mL) and 28% aqueous ammonia (5 mL) were added thereto and the mixture was stirred for 3 hours. The mixture was extracted three times with chloroform, and the combined organic layers were dried over sodium sulfate and concentrated under reduced pressure. The residue was purified by preparative thin layer chromatography (28% aqueous ammonia:methanol:chloroforn=1:9:400), and a free form of a title compound 11 (11.6 mg, 61%) was obtained as a colorless oil material. The free form was converted into a hydrochloride salt in the same manner as in the case of the compound 10, and a title compound 11 was obtained.

(Free Form)

¹H-NMR (400 MHz, CD₂Cl₂) δ (ppm): 0.08-0.18 (m, 2H), 0.45-0.57 (m, 2H), 0.59-0.69 (m, 1H), 0.78-0.94 (m, 2H), 1.17-1.31 (m, 1H), 1.54-1.66 (m, 2H), 1.74 (ddd, J=5.0, 12.6, 12.6 Hz, 1H), 2.23-2.46 (m, 4H), 2.60 (dd, J=5.0, 11.7 Hz, 1H), 3.06 (d, J=18.3 Hz, 1H), 3.45 (d, J=6.4 Hz, 1H), 4.36 (s, 1H), 4.47 (dd, J=6.0, 15.0 Hz, 11H), 4.53 (dd, J=6.0, 15.0 Hz, 1H), 5.95 (br s, 1H), 6.55 (d, J=8.2 Hz, 1H), 6.72 (d, J=8.2 Hz, 1H), 7.22-7.38 (m, 5H), 7.47 (s, 1H), 7.45-7.53 (m, 1H).

Example 3

Synthesis of (4R,4aS,7R,7aR,12bS)-3-(cyclopropylmethyl)-7,9-dihydroxy-N-phenethyl-1,2,3,4,7,7a-hexahydro-4a,7-ethano-4,12-methanobenzofuro[3,2-e]isoquinoline-6-carboxamide hydrochloride (12)

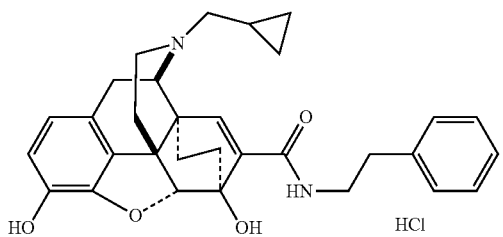

A compound 8 (50 mg, 0.0949 mmol) was dissolved in dichloromethane (2 mL), and then a 1.0 M boron tribromide dichloromethane solution (0.48 mL, 0.480 mmol) was added thereto under ice cooling, and the mixture was stirred at room temperature for 30 minutes. 28% aqueous ammonia (3 mL) was added thereto under ice cooling and the mixture was further stirred at room temperature for 1.5 hours. A saturated sodium hydrogen carbonate aqueous solution (4 mL) was added and extracted 3 times with chloroform. The combined organic layers were dried over sodium sulfate and concentrated under reduced pressure. The residue was purified by silica gel column chromatography (1 to 5% (28% aqueous ammonia:methanol=1:9)/chloroform), and a free form of a title compound 12 (43.5 mg, 92%) was obtained as a colorless oil material. The free form was converted into a hydrochloride salt in the same manner as in the case of the compound 10, and thereby a title compound 12 was obtained.

(Free Form)

¹H-NMR (400 MHz, CDCl₃) δ (ppm): 0.09-0.20 (m, 2H), 0.46-0.60 (m, 2H), 0.61-0.71 (m, 1H), 0.78-0.93 (m, 2H), 1.19-1.30 (m, 1H), 1.55-1.85 (m, 3H), 2.23-2.47 (m, 4H), 2.60 (dd, J=5.0, 11.9 Hz, 1H), 2.89 (t, J=7.2 Hz, 2H), 3.07 (d, J=18.3 Hz, 1H), 3.44 (d, J=6.4 Hz, 1H), 3.56-3.64 (m, 2H), 4.37 (d, J=1.2 Hz, 1H), 5.72 (br s, 1H), 6.56 (d, J=7.8 Hz, 1H), 6.75 (d, J=7.8 Hz, 1H), 6.85-6.98 (m, 1H), 7.19-7.27 (m, 3H), 7.29-7.37 (m, 3H).

Example 4

Synthesis of (4R,4aS,7R,7aR,12bS)-N-benzyl-3-(cyclopropylmethyl)-7,9-dihydroxy-N-methyl-1,2,3,4,7,7a-hexahydro-4a,7-ethano-4,12-methanobenzofuro[3,2-e]isoquinoline-6-carboxamide hydrochloride (13)

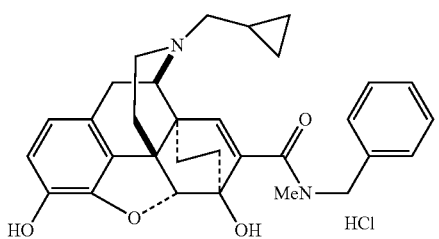

Compound 9 (38.3 mg, 0.0727 mmol) was dissolved in dichloromethane (3 mL), and then a 1.0 M boron tribromide dichloromethane solution (0.36 mL, 0.360 mmol) was added thereto under ice cooling, and the mixture was stirred at room temperature for 1.5 hours. 28% aqueous ammonia (1.3 mL) was further added thereto under ice cooling, and the mixture was further stirred at room temperature for 1.5 hours. A saturated sodium hydrogen carbonate aqueous solution (3 mL) and chloroform (3 mL) were added thereto and the mixture was extracted three times with chloroform. The combined organic layer was dried over sodium sulfate and concentrated under reduced pressure. The residue was purified by preparative thin layer chromatography (28% aqueous ammonia:methanol:chloroform=1:9:300), and a free form of a title compound 13 (36.5 mg, 100%) was obtained as a colorless oil material. The free form was converted into a hydrochloride salt in the same manner as in the case of the compound 10, and thereby a title compound 13 was obtained.

(Free Form)

¹H-NMR (400 MHz, CDCl₃) δ (ppm): 0.01-0.20 (m, 2H), 0.37-0.59 (m, 2H), 0.65-1.05 (m, 3H), 1.23-1.39 (m, 1H), 1.58-1.96 (m, 3H), 2.20-2.48 (m, 4H), 2.49-2.67 (m, 1H), 2.91-3.17 (m, 4H), 3.29 (d, J=5.2 Hz, 0.6H), 3.43 (d, J=5.2 Hz, 0.4H), 4.57 (s, 1H), 4.61-4.99 (m, 3H), 6.50-6.60 (m, 1H), 6.72-6.80 (d, J=8.2 Hz, 1H), 6.84 (s, 1H), 7.25-7.43 (m, 5H).

Reference Example 10

Preparation of Cell Membrane Fraction Samples

Cell membrane fraction samples were prepared from Chinese Hamster Ovary cells (CHO cells) in which each opioid receptor type was stably expressed, respectively. Sufficient opioid receptor-stably expressed CHO cells secured by subculture were separated out by a trypsin treatment, and then formed into cell sediments by centrifugation. The resulting sediments were homogenized under ice cooling in an ice-cold tris buffer (pH 7.4) containing 50 mM tris-HCl, 5 mM MgCl₂ and 1 mM EGTA, and then the suspension was centrifuged (48,000×g, 20 minutes, 4° C.) in a super high speed centrifuge. The resulting sediments were homogenized again in an ice-cold tris buffer (pH 7.4) containing 10% sucrose. After protein determination was performed thereon, the concentration of the resuspension was adjusted to 5,000 µg/mL to prepare a cell membrane sample, and the sample was stored at −80° C. until used for experiments.

Test Example 1

Opioid Receptor Binding Test

In an opioid receptor binding test, [$^3$H] DAMGO (µ opioid receptor), [$^3$H] DPDPE (δ opioid receptor) and [$^3$H] U-69,593 (κ opioid receptor) radioactive ligands (all of these are manufactured by PerkinElmer Co., Ltd., MA, USA) were used as selective ligands for various opioid receptors to perform a test for a binding substitution reaction with a test compound. In the test, a cell membrane sample (75 µg/well) was seeded in a 96-well microplate, each radioactive ligand (each 2 nM) and test compounds at various concentrations were added thereto and incubation was performed at 25° C. and 300 rpm for 2 hours. After the incubation was completed, filtration was performed with a Filtermat B glass filter (PerkinElmer Co., Ltd.) which had been previously soaked in 50 mM tris-HCl (pH 7.4) at 4° C. using a FilterMate cell harvester (Perkin Elmer Co., Ltd.). After filtration, the glass filter was washed three times with 50 mM tris-HCl (pH 7.4), and then the glass filter was dried at 60° C. for 90 minutes using a dryer. After drying, Meltilex B/HS (Perkin Elmer Co., Ltd.) was melted and allowed to infiltrate into the glass filter on a hot plate at 90° C., and the glass filter was put into a clear film case and the case was loaded into the measuring cassette of a Microbeta 2 (PerkinElmer Co., Ltd.). The radioactivity on the glass filter was measured with the Microbeta 2 (PerkinElmer Co., Ltd.), and nonspecific binding was calculated from the difference in binding capacity between in the presence and absence of a nonradioactive ligand (µ: DAMGO, δ: DPDPE, κ: U-69, 593, each 10 µM). The equilibrium inhibition constant (Ki value) obtained by the opioid receptor binding test was calculated by applying an $IC_{50}$ value obtained from the inverse S-shaped curve in the test to the Cheng and Prusoff equation ($Ki=IC_{50}/(1+L/Kd)$) using GraphPad Prism 6 (GraphPad Software, Inc., CA, USA). L in the equation is the concentration of the radioactive ligand, and the dissociation constant Kd value is calculated from the substitution experiment for the radioactive ligand and the nonradioactive ligand.

The results are shown in Table 1.

DAMGO: [D-Ala$^2$,N-MePhe$^4$,Gly-Ol]enkephalin

DPDPE:

[D-Pen$^{2,5}$]-enkephalin hydrate

U-69,593:

(+)-(5α,7α,8β)-N-Methyl-N-[7-(1-pyrrolidinyl)-1-oxaspiro[4.5]dec-8-yl]-benzeneacetamide

TABLE 1

| Compound | Binding affinity (Ki, pM) κ | κ-receptor selectivity (Ki value ratio) | |
|---|---|---|---|
| | | µ/κ | δ/κ |
| Compound 13 (Example 4) | 2.06 | 8.11 | 5.78 |

As shown in Table 1, the compound 13 according to the present invention showed strong affinity for the opioid κ receptor.

Test Example 2

[$^{35}$S] GTPγS binding test

In a [$^{35}$S] GTPγS binding test, the opioid receptor agonist activity of test compounds based on a GTP-GDP exchange reaction was evaluated. In the test, a cell membrane sample (75 µg/well) was seeded in a 96-well microplate, and test compounds at various concentrations, 30 µM guanosine-5'-diphosphate (GDP: Sigma-Aldrich Co., MO. USA) and 100 pM [$^{35}$S] GTPγS (PerkinElmer Co., Ltd.) were added thereto and the incubation was carried out at 300 rpm at 25° C. for 2 hours. After the incubation was completed, filtration was performed with a Filtermat B glass filter (PerkinElmer Co., Ltd.) which had been previously soaked in 50 mM tris-HCl (pH 7.4) at 4° C. using a FilterMate cell harvester (PerkinElmer Co., Ltd.). Following filtration, the glass filter was washed three times with 50 mM tris-HCl (pH 7.4), and then the filter was dried at 60° C. for 90 minutes using a dryer. After drying, Meltilex B/HS (Perkin Elmer Co., Ltd.) was melted and allowed to infiltrate into the glass filter on a hot plate at 90° C., and the glass filter was put into a clear film case and the case was loaded into the measuring cassette of a Microbeta 2 (PerkinElmer Co., Ltd.). The radioactivity on the glass filter was measured with the Microbeta 2 (PerkinElmer Co., Ltd.), and nonspecific binding was calculated from the difference in binding capacity between in the presence and absence of a nonradioactive ligand (10 µM GTPγS: Sigma-AldricH Co.). The 50% effective concentration ($EC_{50}$ value) of the test compound obtained by the [$^{35}$S] GTPγS binding test was calculated from the S-shaped curve obtained by the test using GraphPad Prism 6 (GraphPad Software, Inc., CA, USA).

The results are shown in Table 2.

TABLE 2

| | $EC_{50}$ value (pM) | | |
|---|---|---|---|
| Compound | κ receptor | µ receptor | δ receptor |
| Compound 13 (Example 4) | 2.8 | 2770 | 1700 |

As shown in Table 2, it was confirmed that the compound 13 according to the present invention had potent agonist activity against the opioid κ receptor.

Test Example 3

Acetic Acid Writhing Test

The analgesic effect of the test compound was evaluated by an acetic acid writhing test. In the test, ICR male mice were used and acclimated to plastic open fields for 30 minutes before the test was started. After acclimatization, the test compound (0.3 to 10 µg/kg) or physiological saline was administered subcutaneously (s.c.) to the mice, which were returned to the open fields immediately. After 30 minutes of subcutaneous administration of the test compound, a 0.6% acetic acid aqueous solution was further administered intraperitoneally (i.p.) to the same mouse. From 10 minutes after the administration of the acetic acid aqueous solution, the number of writhing reactions induced in the mouse (writhing response to press the abdominal cavity against the floor and elongate) was measured for 10 minutes, and the analgesic effect of the test compound was evaluated by comparing this number of writhing reactions with that of the control group (physiological saline administered group). The results are shown in Table 3.

TABLE 3

| Compound | Writhing suppression effect ED$_{50}$ value (μg/kg, s.c.) |
| --- | --- |
| Compound 13 (Example 4) | 1.67 |

As shown in Table 3, the compound 13 according to the present invention was determined to show a potent analgesic effect.

Test Example 4

Rotarod Test

The sedative effect (the effect of motor coordination disorder) of the test compound was evaluated by a rotarod test, and mice that had previously acquired motor tasks by rotorrod training were used in the test, and the mice were acclimated for 60 seconds on a rotating shaft rod rotating at 3 rpm (3 cm in diameter, KN-75, Natsume Seisakusho) and repeatedly trained with an appropriate rest period until achieving motor learning. Thereafter, a total of three trainings including 3 rpm for 180 seconds, 4 rpm for 180 seconds, and 5 rpm for 180 seconds were provided. After all the training, a rest for 90 to 120 minutes was provided to reduce the burden on the mice. Further, mice that were not able to achieve motor learning even by training were not used for the experiments. In the rotarod test, the total number of dropping times and the residence time on the rotating shaft bar until the first drop at 5 rpm for 300 seconds (cut-off value of 300 seconds) were measured as preliminary values before the administration of the test compound. After measuring the preliminary values, the mouse was treated with the test compound (1 to 30 μg/kg) or physiological saline subcutaneously (sc), and the sedative effect of the test compound 120 minutes after the administration of the test compound was evaluated by the total number of dropping times at 8 rpm for 300 seconds. The results are shown in FIG. 1.

As shown in FIG. 1, the compound 13 according to the present invention was determined to show no sedative effect as compared with nalfurafine.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A morphinan derivative represented by the following formula (I), a tautomer or a stereoisomer of the compound, a pharmaceutically acceptable salt thereof or a solvate thereof:

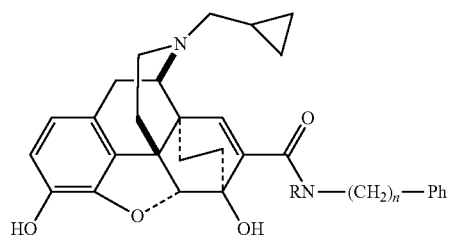

(I)

wherein R is selected from hydrogen and C$_{1-6}$ alkyl, and n represents an integer of 0 to 2.

2. A compound selected from
(a) (4R,4aS,7R,7aR,12bS)-3-(cyclopropylmethyl)-7,9-dihydroxy-N-phenyl-1,2,3,4,7,7a-hexahydro-4a,7-ethano-4,12-methanobenzofuro[3,2-e]isoquinoline-6-carboxamide,
(b) (4R,4aS,7R,7aR,12bS)-N-benzyl-3-(cyclopropylmethyl)-7,9-dihydroxy-1,2,3,4,7,7a-hexahydro-4a,7-ethano-4,12-methanobenzofuro[3,2-e]isoquinoline-6-carboxamide,
(c) (4R,4aS,7R,7aR,12bS)-3-(cyclopropylmethyl)-7,9-dihydroxy-N-phenethyl-1,2,3,4,7,7a-hexahydro-4a,7-ethano-4,12-methanobenzofuro[3,2-e]isoquinoline-6-carboxamide, and
(d) (4R,4aS,7R,7aR,12bS)-N-benzyl-3-(cyclopropylmethyl)-7,9-dihydroxy-N-methyl-1,2,3,4,7,7a-hexahydro-4a,7-ethano-4,12-methanobenzofuro[3,2-e]isoquinoline-6-carboxamide,
a tautomer or a stereoisomer of the compound, a pharmaceutically acceptable salt thereof or a solvate thereof.

3. A pharmaceutical composition containing a morphinan derivative, a tautomer or a stereoisomer of the compound, a pharmaceutically acceptable salt thereof or a solvate thereof according to claim 1 as an active ingredient.

4. A pharmaceutical composition containing a morphinan derivative, a tautomer or a stereoisomer of the compound, a pharmaceutically acceptable salt thereof or a solvate thereof according to claim 2 as an active ingredient.

5. The pharmaceutical composition according to claim 3, which is an agent for treating or ameliorating cardiovascular disorders, digestive system diseases, blood system diseases, respiratory diseases, liver diseases, nervous system disorders, urinary system disorders, pain, cough, pruritus, ischemic brain diseases, or drug dependence.

6. The pharmaceutical composition according to claim 4, which is an agent for treating or ameliorating cardiovascular disorders, digestive system diseases, blood system diseases, respiratory diseases, liver diseases, nervous system disorders, urinary system disorders, pain, cough, pruritus, ischemic brain diseases, or drug dependence.

7. The pharmaceutical composition according to claim 3, which is an analgesic.

8. The pharmaceutical composition according to claim 4, which is an analgesic.

9. The pharmaceutical composition according to claim 5, which is an analgesic.

10. The pharmaceutical composition according to claim 6, which is an analgesic.

11. The pharmaceutical composition according to claim 3, which is an antipruritic drug.

12. The pharmaceutical composition according to claim 4, which is an antipruritic drug.

13. The pharmaceutical composition according to claim 5, which is an antipruritic drug.

14. The pharmaceutical composition according to claim 6, which is an antipruritic drug.

15. A method for treating or ameliorating cardiovascular disorders, digestive system diseases, blood system diseases, respiratory diseases, liver diseases, nervous system disorders, urinary system disorders, pain, cough, pruritus, ischemic brain diseases, or drug dependence,
the method comprising:
administering a therapeutically effective amount of the compound of claim 1, a tautomer or a stereoisomer of the compound, a pharmaceutically acceptable salt thereof or a solvate thereof to a person in need thereof.

* * * * *